United States Patent [19]

Hussain et al.

[11] 4,315,925

[45] Feb. 16, 1982

[54] METHOD OF ADMINISTERING NATURAL FEMALE SEX HORMONES

[75] Inventors: Anwar A. Hussain; Shinichiro Hirai; Rima Bawarshi, all of Lexington, Ky.

[73] Assignee: University of Kentucky Research Foundation, Lexington, Ky.

[21] Appl. No.: 154,995

[22] Filed: May 30, 1980

[51] Int. Cl.$^3$ .......................................... A01N 45/00
[52] U.S. Cl. ....................................................... 424/239
[58] Field of Search ......................................... 424/239

[56] References Cited

U.S. PATENT DOCUMENTS

| | | | |
|---|---|---|---|
| 3,733,407 | 5/1973 | Segre | 424/239 |
| 3,942,641 | 3/1976 | Segre | 424/239 |
| 4,071,623 | 1/1978 | van der Vies | 424/239 |
| 4,145,416 | 3/1979 | Lachnit-Fixson et al. | 424/239 |

OTHER PUBLICATIONS

Brown et al., "British Medical Journal", Mar. 4, 1972, pp. 585-590.

Primary Examiner—Elbert L. Roberts
Attorney, Agent, or Firm—Burns, Doane, Swecker & Mathis

[57] ABSTRACT

The invention relates to a novel method of administering the natural female sex hormones, 17 $\beta$- estradiol and progesterone, to achieve enhanced bioavailability thereof. The invention further relates to novel dosage forms of 17 $\beta$- estradiol and/or progesterone which are adapted for nasal administration, such as solutions, suspensions, gels and ointments. The dosage forms containing a combination of 17 $\beta$-estradiol and progesterone are particularly useful as contraceptives, while the dosage forms containing only one of the hormonal components find utility in the treatment of conditions such as menopause, menstrual disorders, etc., which are known to respond to administration of a natural or synthetic female hormone.

20 Claims, 5 Drawing Figures

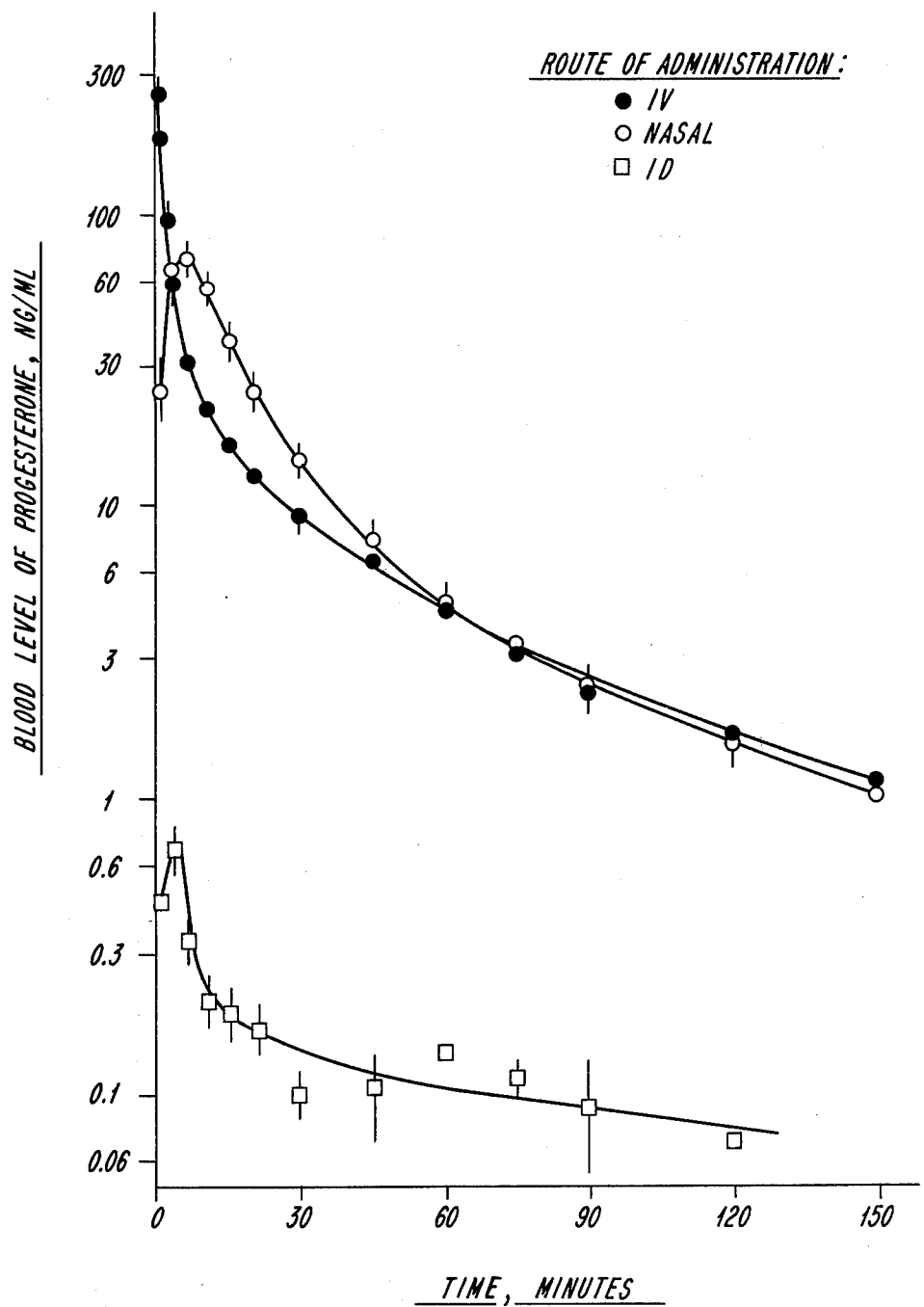

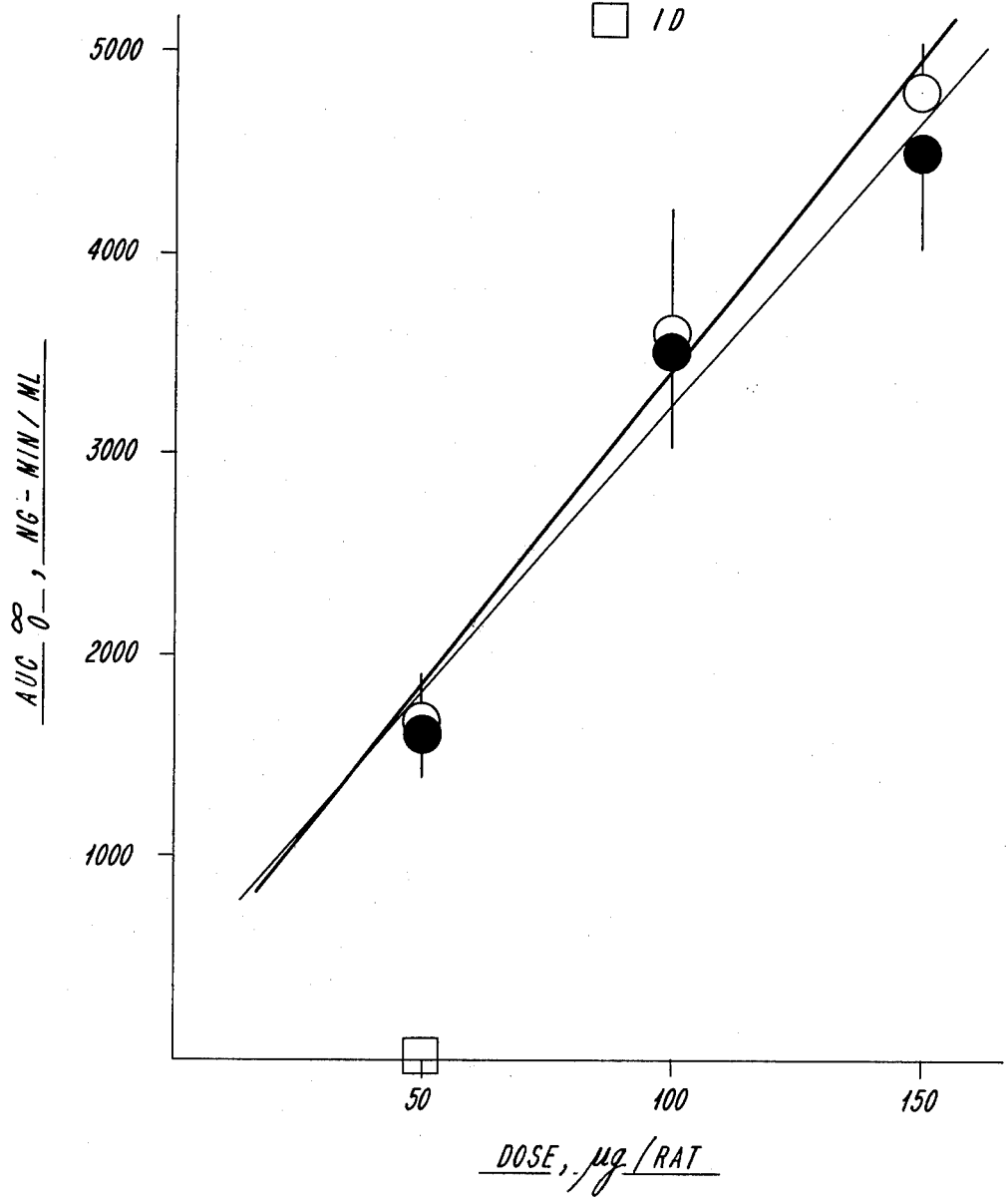

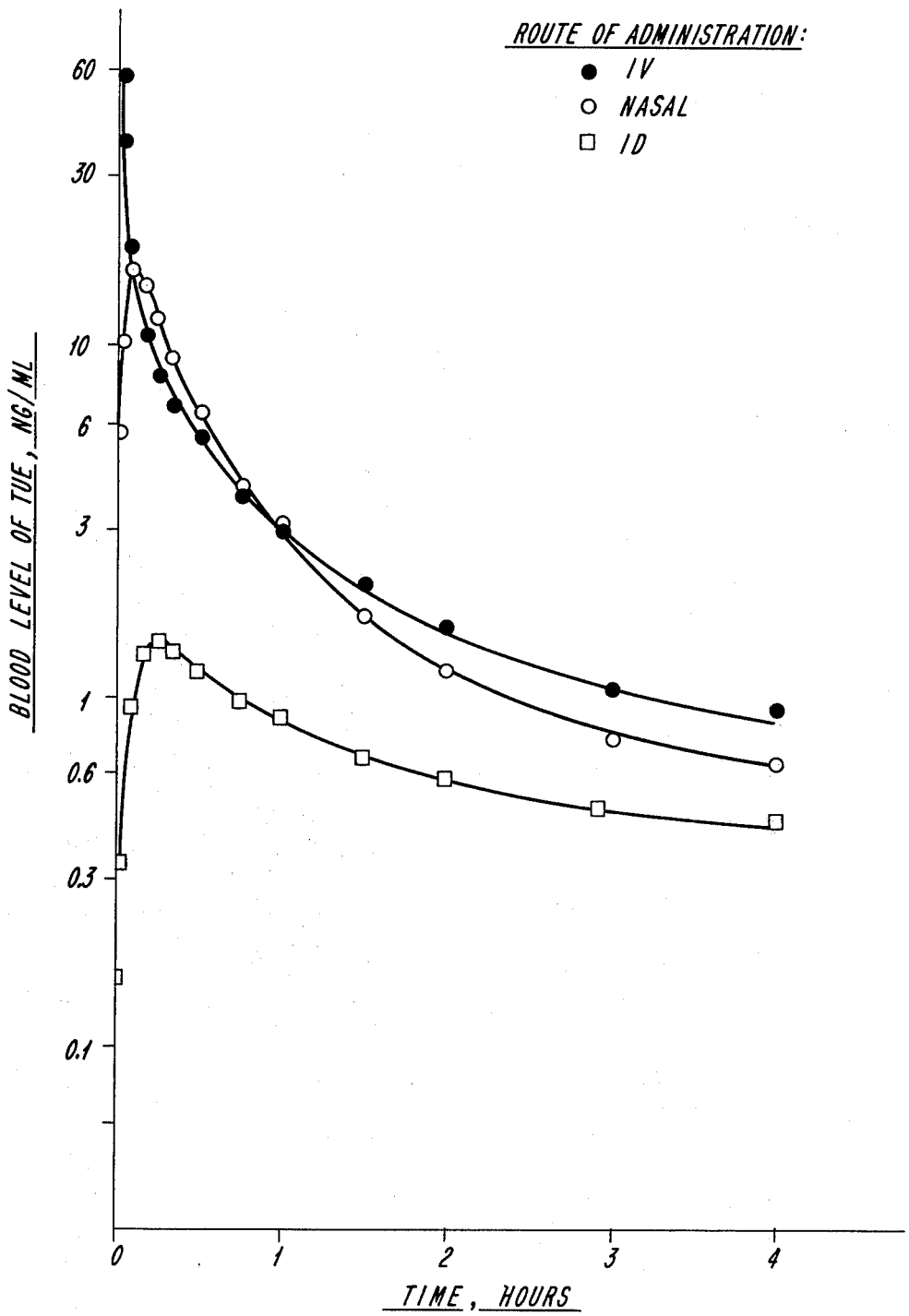

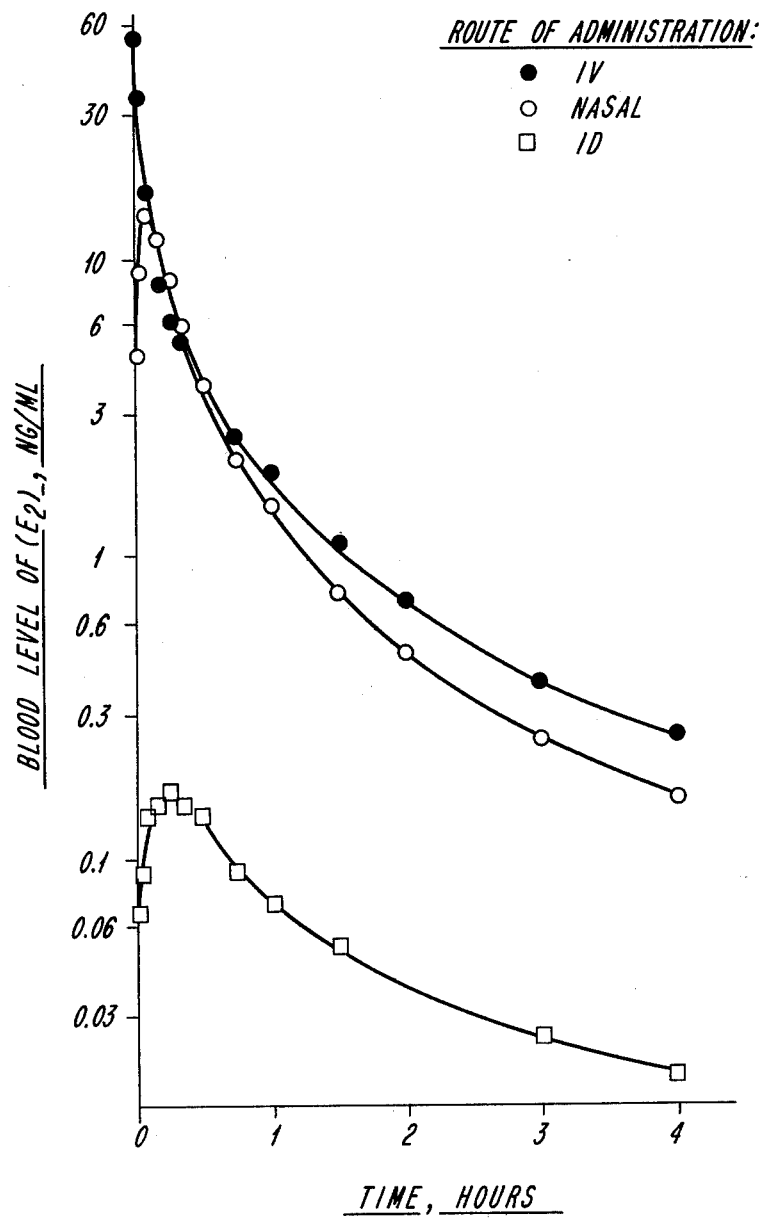

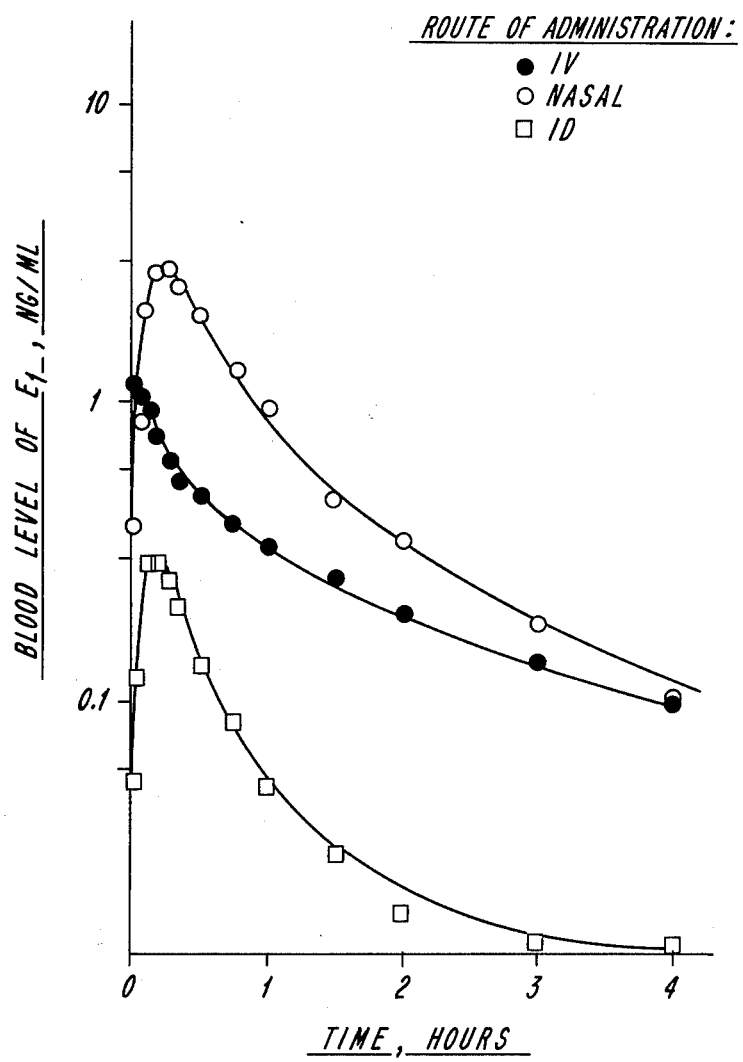

METHOD OF ADMINISTERING NATURAL FEMALE SEX HORMONES

BACKGROUND OF THE INVENTION

1. Field of the Invention

The present invention relates to a novel method of administering the natural female sex hormones, 17β-estradiol and progesterone, and to novel dosage forms containing those compounds, singly or in combination, which are adapted for nasal administration.

2. Description of the Prior Art

17β-estradiol is the most potent natural estrogen found in human beings and is the major secretory product of the ovary. It is readily oxidized in the body to estrone, which in turn can be hydrated to estriol. These transformations take place mainly in the liver, where there is free interconversion between estrone and estradiol. All three of these natural estrogens are excreted in the urine as glucuronides and sulfates, along with a host of related, minor products in water-soluble complexes. It is widely known that, following oral administration of micronized 17β-estradiol ($E_2$), the incremental circulation estrogen is principally the less active species estrone ($E_1$), which reaches a peak concentration many times greater than that of $E_2$. The conversion of $E_2$ to $E_1$ and subsequently to other metabolites takes place during absorption from the intestine and passage through the liver. This extensive metabolism greatly limits the oral effectiveness of the natural estrogens and their esters. Indeed, because of their limited oral efficacy, 17β-estradiol and its esters are generally administered by intramuscular injection.

Progesterone is the active natural progestin which occurs in the corpus luteum, placenta and adrenal cortex. It is not effective by mouth because of its rapid metabolism in the intestinal epithelium and in the liver, and is therefore only administered intramuscularly.

Because of their limited oral effectiveness, these natural female sex hormones have not found utility in oral contraceptives. Instead, only active synthetic estrogens and progestins have been prepared and are used for contraceptive purposes. The synthetic derivatives have also in many cases replaced the natural substances in the treatment of menopause, threatened abortion, etc. However, the synthetic derivatives are, generally speaking, much more likely to cause toxic side effects than are the relatively safe natural hormones.

SUMMARY OF THE INVENTION

In view of the foregoing, it is apparent that a serious need exists for the improved delivery of the natural female sex hormones. Thus, it is an object of the present invention to provide novel dosage forms and a novel method of administering 17β-estradiol and progesterone, separately or in combination, which will provide greatly enhanced bioavailability as compared to oral administration, while at the same time providing relative ease of administration when compared to intramuscular injection.

It is a further object of the present invention to provide a novel contraceptive method and novel compositions for accomplishing same which utilize the natural female sex hormones, 17β-estradiol and progesterone, and thus avoid the disadvantages inherent in the use of potentially unsafe synthetic estrogens and progestins.

It is yet a further object of the present invention to provide a novel method and novel dosage forms containing 17β-estradiol or progesterone useful in the treatment of conditions such as menopause, menstrual disorders, etc. which are known to respond to administration of a natural or synthetic female sex hormone.

The foregoing objects are achieved by nasal administration of 17β-estradiol (if desired, in the form of one of its estrogenically effective esters) and/or progesterone. According to the invention, these natural female sex hormones are administered via a novel nasal dosage form, i.e., a solution, suspension, ointment or gel adapted for nasal administration.

BRIEF DESCRIPTION OF THE DRAWINGS

FIG. 1 is a semi-logarithmic plot of mean blood levels of progesterone after intravenous (IV), nasal and intraduodenal/oral (ID) administration of a dose of 50 μg of progesterone per rat.

FIG. 2 is a graph showing the area under the curve as a function of dose for the intravenous (IV) and nasal routes of progesterone administration (50 μg, 100 μg and 150 μg dosage levels).

FIG. 3 is a semi-logarithmic plot of mean blood levels of total unconjugated estrogens (TUE) following intravenous (IV), nasal and intraduodenal/oral (ID) administration of a dose of 10 μg of 17β-estradiol per rat.

FIG. 4 is a semi-logarithmic plot of mean blood levels of estradiol ($E_2$) following intravenous (IV), nasal and intraduodenal/oral (ID) administration of a dose of 10 μg of 17β-estradiol per rat.

FIG. 5 is a semi-logarithmic plot of mean blood levels of estrone ($E_1$) following intravenous (IV), nasal and intraduodenal/oral (ID) administration of a dose of 10 μg of 17β-estradiol per rat.

DETAILED DESCRIPTION OF THE INVENTION

The word "progesterone" as used herein means pregn-4-ene-3,20-dione, i.e., the compound of the formula

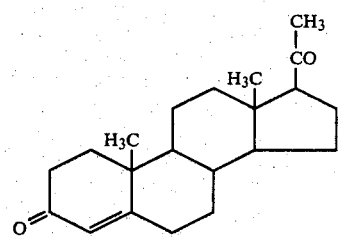

and is intended to include progesterone derived from natural sources as well as that made synthetically.

The word "17β-estradiol" as used herein is intended to encompass any pharmaceutically acceptable, estrogenically active form of 17β-estradiol, i.e., estra-1,3,5(10)-triene-3,17β-diol itself, which has the formula

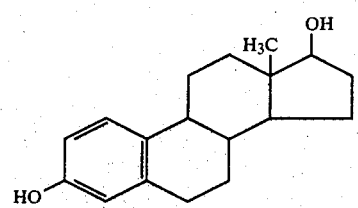

and which may be extracted from natural sources or made synthetically, or one of its 3- or 17-monoesters or 3,17-diesters. By way of illustration, suitable esters of 17β-estradiol for purposes of the present invention include 3-monoesters such as estradiol benzoate and estradiol 3-acetate; 17-monoesters such as estradiol cypionate, estradiol 17-propionate, estradiol 17-acetate, estradiol 17-heptanoate (estradiol enanthate), estradiol 17-undecanoate (estradiol undecylate) and estradiol 17-valerate; and 3,17-diesters such as estradiol dipropionate and estradiol diacetate.

According to the present invention, it has surprisingly been found that 17β-estradiol and progesterone can be administered nasally with results considerably superior to those obtained with oral administration. The following studies were undertaken to examine the bioavailability of progesterone and 17β-estradiol from nasal solution in comparison with the bioavailability of these drugs when administered orally and intravenously.

Sprague-Dawley male rats, each weighing about 270 grams, were used in the progesterone study. For nasal administration, the rats were anesthetized using sodium pentobarbital (50 mg/kg) and the drug was administered to the nasal cavity by means of a micropipet at dosage levels of 50 μg, 100 μg and 150 μg/rat of [4-$^{14}$C]-progesterone (~8.5 μCi/rat) in 0.1 ml of isotonic saline containing 1-2% Tween 80 as a solubilizing agent, according to the procedure described by Hirai et al, the 98th Annual Meeting of Pharmaceutical Society of Japan, Okayama, April 1978, except that the end of the tube leading from the esophagus to the nasal cavity was closed and the drug was administered to the nostrils which were then closed with an adhesive agent. For oral (intraduodenal) administration, the rats were anesthetized and the abdomen of each rat was opened through a midline incision and a 50 μg/rat dose of the drug ([4-$^{14}$C]-progesterone in 0.1 ml isotonic saline with 1-2% Tween 80) was injected directly through the duodenum. For intravenous administration, the rats were anesthetized and the drug was injected through the femoral vein at dosage levels of 50 μg, 100 μg and 150 μg/rat of [4-$^{14}$C]-progesterone in 0.1 ml of isotonic saline containing 1-2% Tween 80. Blood was sampled periodically from the femoral aorta after IV and nasal administration, and from the tail vein after ID administration. Blood levels of progesterone were determined by thin layer chromotography.

FIG. 1 shows the mean blood levels of progesterone for the study described above after intravenous, nasal and oral administration of a dose of 50 μg/rat, while Table I below summarizes the area under the curve for the three routes of administration at the various doses.

TABLE I

AREA UNDER THE CURVE AFTER INTRAVENOUS, NASAL AND INTRADUODENAL ADMINISTRATION OF PROGESTERONE IN RATS

| Dose μg/rat | $AUC_0^\infty$, ng.min/ml | | | Nasal IV | ID IV |
|---|---|---|---|---|---|
| | IV | Nasal | ID | | |
| 50 | 1612.2* ±80.8 | 1659.0 ±109.2 | 19.0 ±4.6 | 1.029 | 0.012 |
| 100 | 3520.0 ±491.0 | 3599.0 ±621.4 | — | 1.022 | — |
| 150 | 4480.2 ±466.4 | 4798.9 ±188.5 | — | 1.071 | — |

*mean ± SE(n = 4-6).

By using the two tailed t-test, it can be shown that the area under the curve following intravenous and nasal administration at each dosage were not significantly different, even at the 0.001 level. However, as can be seen from Table I, oral administration of 50 μg resulted in bioavailability equal to only 1.2% that of an equivalent dose given intravenously. Also from Table I, it can be seen that the nasal bioavailability of progesterone at the 50 μg dosage level was 85.75 times greater than the oral bioavailability.

It can also be seen from FIG. 1 that progesterone is very rapidly absorbed from the nasal mucosa; thus, at the 50 μg dosage level, the peak plasma level was attained in less than 7 minutes after instillation of the nose drops.

FIG. 2 shows the area under the curve as a function of dose for the intravenous and nasal routes. As can be seen from FIG. 2, for both IV and nasal routes of administration the area under the curve (AUC) was directly proportional to the dose administered.

The study described above indicates that progesterone is rapidly absorbed from the nasal mucosa into the systemic circulation without first pass metabolism. It is further apparent from this study that the bioavailability of progesterone when administered nasally is equivalent to the bioavailability of the drug where administered intravenously and vastly superior to its bioavailability by the oral route.

A study similar to that described above was undertaken to study the bioavailability of nasally administered 17β-estradiol vis-a-vis its bioavailability via intravenous and oral routes. Sprague-Dawley male rats, each weighing approximately 270 grams, were given dosages of 5 μg, 10 μg and 20 μg/rat of [6,7-$^3$H] 17β-estradiol in 0.1 ml isotonic saline containing 1% Tween 80 via the intravenous, nasal and intraduodenal routes, according to the procedures described above with respect to the progesterone study. Blood samples were taken periodically as described in the progesterone study and assayed for estradiol ($E_2$), estrone ($E_1$) and total unconjugated estrogens (TUE).

FIGS. 3, 4 and 5 show typical plots of the mean blood levels of TUE, $E_2$ and $E_1$ following intravenous, nasal and oral administration of 10 μg of 17β-estradiol per rat. These figures clearly show that 17β-estradiol is rapidly absorbed by the nasal mucosa.

Table II below shows the area under the curve for the three routes of administration at the various dosage levels of 17β-estradiol.

TABLE II

AREA UNDER THE CURVE AND BIOAVAILABILITY OF TUE, $E_2$ AND $E_1$ FOR THE DIFFERENT ROUTES OF ADIMINISTRATION AT THE VARIOUS DOSES

| DOSE μG/RAT | ROUTE OF ADMINISTRATION | $AUC_0^\infty$, NG. MIN. ML$^{-1}$ | | |
|---|---|---|---|---|
| | | TUE | $E_2$ | $E_1$ |
| 5 | IV | 555.5 | 290.8 | 53.4 |
| | NASAL | 337.0 | 146.8 | 88.5 |
| | | (0.606) | (0.505) | (1.657) |
| | ORAL | 119.2 | 11.1 | 10.6 |
| | | (0.215) | (0.038) | (0.199) |
| 10 | IV | 954.6 | 609.0 | 83.5 |
| | NASAL | 761.2 | 415.2 | 173.1 |
| | | (0.797) | (0.682) | (2.073) |
| | ORAL | 314.2 | 19.1 | 16.8 |
| | | (0.329) | (0.031) | (0.201) |
| 20 | IV | 1936.9 | 1062.6 | 164.4 |
| | NASAL | 1777.2 | 891.8 | 354.0 |
| | | (0.918) | (0.839) | (2.153) |
| | ORAL | 786.9 | 53.4 | 42.4 |

TABLE II-continued

AREA UNDER THE CURVE AND BIOAVAILABILITY OF TUE, $E_2$ AND $E_1$ FOR THE DIFFERENT ROUTES OF ADIMINISTRATION AT THE VARIOUS DOSES

| DOSE µG/RAT | ROUTE OF ADMINISTRATION | $AUC_0^\infty$, NG. MIN. $ML^{-1}$ | | |
|---|---|---|---|---|
| | | TUE | $E_2$ | $E_1$ |
| | | (0.406) | (0.050) | (0.258) |

( ) RATIO VS. IV

As can be seen from Table II, the TUE bioavailability after nasal administration ranged from 60.6% to 91.8% that of the corresponding doses given intravenously, while oral administration resulted in TUE bioavailability that ranged from only 21.5% to 40.6% that of the corresponding doses given intravenously. Thus, nasal bioavailability of TUE was from 2.26 to 2.83 times greater than oral bioavailability. Even more significantly, Table II further shows that the $E_2$ bioavailability after nasal administration ranged from 50.5% to 83.9% that of the corresponding doses given intravenously, while oral administration resulted in $E_2$ bioavailabilities that ranged from only 3.1% to 5.0% that of the corresponding doses given intravenously. Thus, nasal bioavailability of $E_2$ was from 13.23 to 21.74 times greater than oral bioavailability.

The studies described above indicate that progesterone and 17 β-estradiol are rapidly absorbed from the nasal mucosa into systemic blood without extensive intestinal or first pass metabolism.

Progesterone and 17β-estradiol can be conveniently administered nasally to warm-blooded animals by formulating them, singly or in combination, into a nasal dosage form comprising the selected natural female sex hormone(s) and a nontoxic pharmaceutically acceptable nasal carrier therefor. As indicated earlier, any pharmaceutically acceptable, estrogenically active form of 17β-estradiol can be employed in the nasal form, e.g., the diol itself or one of its esters. In a preferred embodiment of the invention, both progesterone and a suitable form of 17β-estradiol are present in the nasal dosage form, which can be employed in preventing conception, for example, by administration in a cyclic manner analagous to that used for the oral contraceptives.

In another embodiment, the estrogenic component, i.e., one of the suitable forms of 17β-estradiol, is present but progesterone is not; this type of composition may be used for any of a variety of conditions for which natural or synthetic estrogens have previously been administered, e.g., to control menopausal symptoms, hot flushes and later osteoporosis; also in atropic vaginitis, and to relieve postpartum breast engorgement, dysmenorrhea, amenorrhea, menorrhagia, and as substitution therapy in ovarian dwarfism; also to control prostatic carcinoma, and possibly also as a "morning-after" contraceptive. Also, the "estrogen only" nasal composition could be used in a sequential contraceptive regimen in which estrogen alone is to be administered for a part of the cycle.

In another embodiment of the present invention, progesterone is present in the nasal dosage form, but the estrogenic component is not. This type of composition may be used in the treatment of conditions for which natural or synthetic progestins have previously been used, e.g., in threatened or habitual abortion, endometriosis and menstrual disorders such as dysmenorrhea and functional uterine bleeding, in inhibiting ovulation and possibly as a "progestin only" continuously administered contraceptive (analogous to "minipill" type of oral contraceptives).

Suitable nontoxic pharmaceutically acceptable nasal carriers for use in the compositions of the present invention will be apparent to those skilled in the art of nasal pharmaceutical formulations. For those not skilled in the art, reference is made to the text entitled "REMINGTON'S PHARMACEUTICAL SCIENCES", 4th edition, 1970. Obviously, the choice of suitable carriers will depend on the exact nature of the particular nasal dosage form desired, e.g. whether the active ingredient(s) is/are to be formulated into a nasal solution (for use as drops or as a spray), a nasal suspension, a nasal ointment or a nasal gel, as well as on the identity of the active ingredient(s). Preferred nasal dosage forms are solutions, suspensions and gels, which contain a major amount of water (preferably purified water) in addition to the active ingredient(s). Minor amounts of other ingredients such as pH adjusters (e.g., a base such as NaOH), emulsifiers or dispersing agents (e.g. polyoxyethylene 20 sorbitan mono-oleate), buffering agents, preservatives, wetting agents and jelling agents (e.g. methylcellulose) may also be present. Also, a sustained release composition, e.g. sustained release gel, readily can be prepared by employing 17β-estradiol in one of its relatively insoluble, long-acting forms, e.g. as estradiol cypionate.

Examples of the preparation of typical nasal compositions are set forth below. However, it is to be understood that these examples are given by way of illustration only and are not to be construed as limiting the invention either in spirit or in scope as many modifications both in materials and in methods will be apparent to those skilled in the art.

EXAMPLE 1

25 milligrams of progesterone and 5 milligrams of 17β-estradiol were combined with 10 milligrams of Tween 80. That mixture was then combined with a quantity of isotonic saline sufficient to bring the total volume to 50 milliliters. The solution was sterilized by being passed through a 0.2 micron Millipore filter.

EXAMPLE 2

50 milligrams of progesterone and 5 milligrams of 17 β-estradiol were combined with 10 milligrams of Tween 80. That mixture was then combined with a quantity of isotonic saline sufficient to bring the total volume of the solution to 50 milliliters. The solution was sterilized by being passed through a 0.2 micron Millipore filter.

EXAMPLE 3

250 milliliters of isotonic saline were heated to 80° C. and 1.50 grams of Methocel were added, with stirring. The resultant mixture was allowed to stand at room temperature for 2 hours. Then, 50 milligrams of progesterone and 10 milligrams of 17β-estradiol were mixed together with 10 milligrams of Tween 80. The steroid/Tween mixture and a quantity of isotonic saline sufficient to bring the total volume to 500 milliliters were added to the gel and thoroughly mixed.

EXAMPLE 4

Repetition of the procedure of Example 1, but omitting the 25 milligrams of progesterone, affords an "estrogen only" nasal composition.

EXAMPLE 5

Repetition of the procedure of Example 2, but omitting the 5 milligrams of 17β-estradiol, affords a "progesterone only" nasal composition.

EXAMPLE 6

Substitution of an equivalent quantity of estradiol benzoate, estradiol cypionate, estradiol dipropionate, estradiol enanthate or estradiol 17-valerate for the 17β-estradiol employed in Example 1, 2, 3 or 4 and repetition of the procedures there detailed affords other nasal compositions according to the invention.

Naturally, the therapeutic dosage range for nasal administration of the compositions of the present invention will vary with the size of the patient, the condition for which the composition is administered and the particular form of 17β-estradiol employed (when the composition is an "estrogen only" or estrogen/progestin combination). A typical dose of a combination form for use as a contraceptive would be from 10 μg to 500 μg of 17β-estradiol and from 10 μg to 5000 μg of progesterone, administered nasally once daily. The quantity of nasal dosage form needed to deliver the desired dose will of course depend on the concentration of the active ingredients in the composition. For example, when a composition as described in Example 2 above is used to deliver a typical dose of 0.5 mg of progesterone, the volume of solution which would be needed would be approximately 0.5 ml.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method of mammalian contraception which comprises nasally administering to a female mammal a contraceptively effective amount of a combination of progesterone and a pharmaceutically acceptable, estrogenically active form of 17β-estradiol.

2. A method of eliciting a progestational response in a mammal which comprises nasally administering thereto a progestationally effective amount of progesterone.

3. A method of eliciting an estrogenic response in a mammal which comprises nasally administering thereto an estrogenically effective amount of a pharmaceutically acceptable, estrogenically active form of 17β-estradiol.

4. A method of mammalian contraception according to claim 1 which comprises nasally administering to a female mammal a pharmaceutically acceptable nasal dosage form which comprises a contraceptively effective amount of a combination of progesterone and a pharmaceutically acceptable, estrogenically active form of 17β-estradiol, together with a nontoxic pharmaceutically acceptable nasal carrier therefor.

5. A method according to claim 2 for eliciting a progestational response in a mammal which comprises nasally administering thereto a pharmaceutically acceptable nasal dosage form which comprises a progestationally effective amount of progesterone and a nontoxic pharmaceutically acceptable nasal carrier therefor.

6. A method according to claim 3 for eliciting an estrogenic response in a mammal which comprises nasally administering thereto a pharmaceutically acceptable nasal dosage form which comprises an estrogenically effective amount of a pharmaceutically acceptable, estrogenically active form of 17β-estradiol and a nontoxic pharmaceutically acceptable nasal carrier therefor.

7. A method according to claim 1, 3, 4 or 6 wherein the pharmaceutically acceptable, estrogenically active form of 17β-estradiol is selected from the group consisting of 17β-estradiol, 3-monoesters of 17β-estradiol, 17-monoesters of 17β-estradiol and 3,17-diesters of 17β-estradiol.

8. A method according to claim 7 wherein the pharmaceutically acceptable, estrogenically active form of 17β-estradiol is 17β-estradiol.

9. A method according to claim 7 wherein the pharmaceutically acceptable, estrogenically active form of 17β-estradiol is estradiol benzoate.

10. A method according to claim 7 wherein the pharmaceutically acceptable, estrogenically active form of 17β-estradiol is estradiol cypionate.

11. A method according to claim 7 wherein the pharmaceutically acceptable, estrogenically active form of 17β-estradiol is estradiol dipropionate.

12. A method according to claim 7 wherein the pharmaceutically acceptable, estrogenically active form of 17β-estradiol is estradiol enanthate.

13. A method according to claim 7 wherein the pharmaceutically acceptable, estrogenically active form of 17β-estradiol is estradiol 17-valerate.

14. A method according to claim 4, 5 or 6 wherein said dosage form is a nasal solution.

15. A method according to claim 4, 5 or 6 wherein said dosage form is a nasal suspension.

16. A method according to claim 4, 5 or 6 wherein said dosage form is a nasal ointment.

17. A method according to claim 4, 5 or 6 wherein said dosage form is a nasal gel.

18. A method according to claim 4 or 6 wherein said dosage form is a sustained release nasal dosage form.

19. A method according to claim 4 or 6 wherein said dosage form is a sustained release nasal gel.

20. A method according to claim 4, 5 or 6 wherein said dosage form is isotonic.

* * * * *